United States Patent [19]
Chan et al.

[11] Patent Number: 5,874,235
[45] Date of Patent: Feb. 23, 1999

[54] SCREENING ASSAYS FOR CANCER CHEMOPREVENTATIVE AGENTS

[75] Inventors: Timothy A. Chan, Baltimore; Patrice J. Morin, Cockeysville; Bert Vogelstein, Baltimore; Kenneth W. Kinzler, Belair, all of Md.

[73] Assignee: The Johns Hopkins University

[21] Appl. No.: 896,462

[22] Filed: Jul. 18, 1997

[51] Int. Cl.⁶ .............................. C12Q 1/34; C12Q 1/00; C12Q 1/42
[52] U.S. Cl. .............................. 435/18; 435/4; 435/7.21; 435/7.23; 435/19; 435/21; 436/63
[58] Field of Search .............................. 435/18, 4, 7.21, 435/7.23, 19, 21, 63

[56] References Cited

U.S. PATENT DOCUMENTS 5,530,114   6/1996   Bennett et al. .............................. 435/18

OTHER PUBLICATIONS

Giardiello et al; Europe. Jour. of Cancer, vol. 31A, Nos. 7/8 pp. 1071–1076; 1995.
Kelloff et al; Jour. of Cellular Biochem; vol. 265, pp. 54–71; 1996.
Marks et al; Toxicology Letters, vol. 82/83, pp. 907–917; (1995).
Steele et al; Jour of Cellular Biochem; vol. 265, pp. 29–53; (1996).
Tepper et al., "Role for ceramide as an endogenous mediator of Fasinduced cytotoxiicity" Proc. Natl. Acad. Sci., USA, vol. 92, pp. 8443–8447, Aug. 1995.
Bose et al., "Ceramide Synthase Mediates Daunorubicin–Induced Apoptosis: An Alternative Mechanism for Generating Death Signals" Cell, vol. 82, 405–414, Aug. 11, 1995.
Jayadev et al., "Identification of Arachidonic Acid as a Mediator of Sphingomyelin Hydrolysis in Response to Tumor Necrosis Factor a", The Journal of Biological Chemistry, vol. 269, No. 8, pp. 5757–5763, Feb. 25, 1994.
Obeid et al., "Programmed Cell Death Induced by Ceramide", Science, vol. 259, pp. 1769–1771, Mar. 19, 1993.
Jarvis et al., "Induction of apoptotic DNA damage and cell death by activation of the sphingmyelin pathway" Proc. Natl. Acad. Sci. vol. 92 pp. 73–77, Jan. 1994.

*Primary Examiner*—Louise N. Leary
*Attorney, Agent, or Firm*—Banner & Witcoff, Ltd.

[57]    ABSTRACT

Nonsteroidal anti-inflammatory drugs cause a dramatic increase in intracellular ceramide, which induces apoptosis. The ceramide increase is likely mediated by cyclooxygenase inhibition, which elevates arachidonic acid, which stimulates sphingomyelinase, which produces ceramide. Contacting members of this pathway with test compounds and observing their effects provides a method of screening for potential cancer chemopreventative agents.

28 Claims, 11 Drawing Sheets

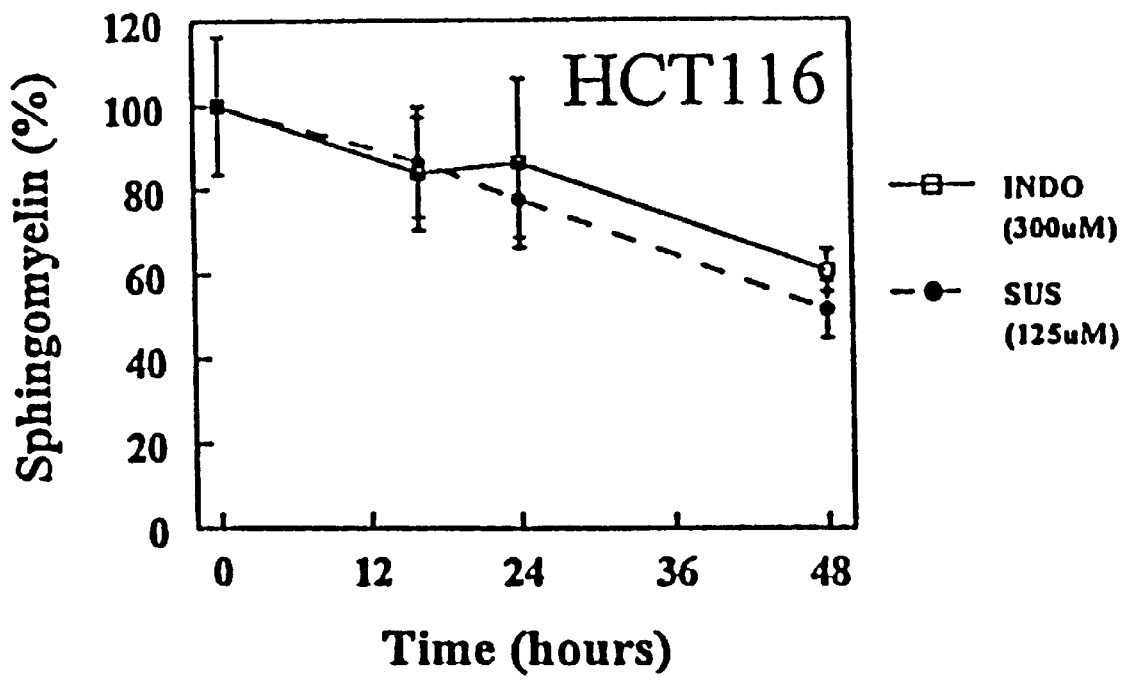
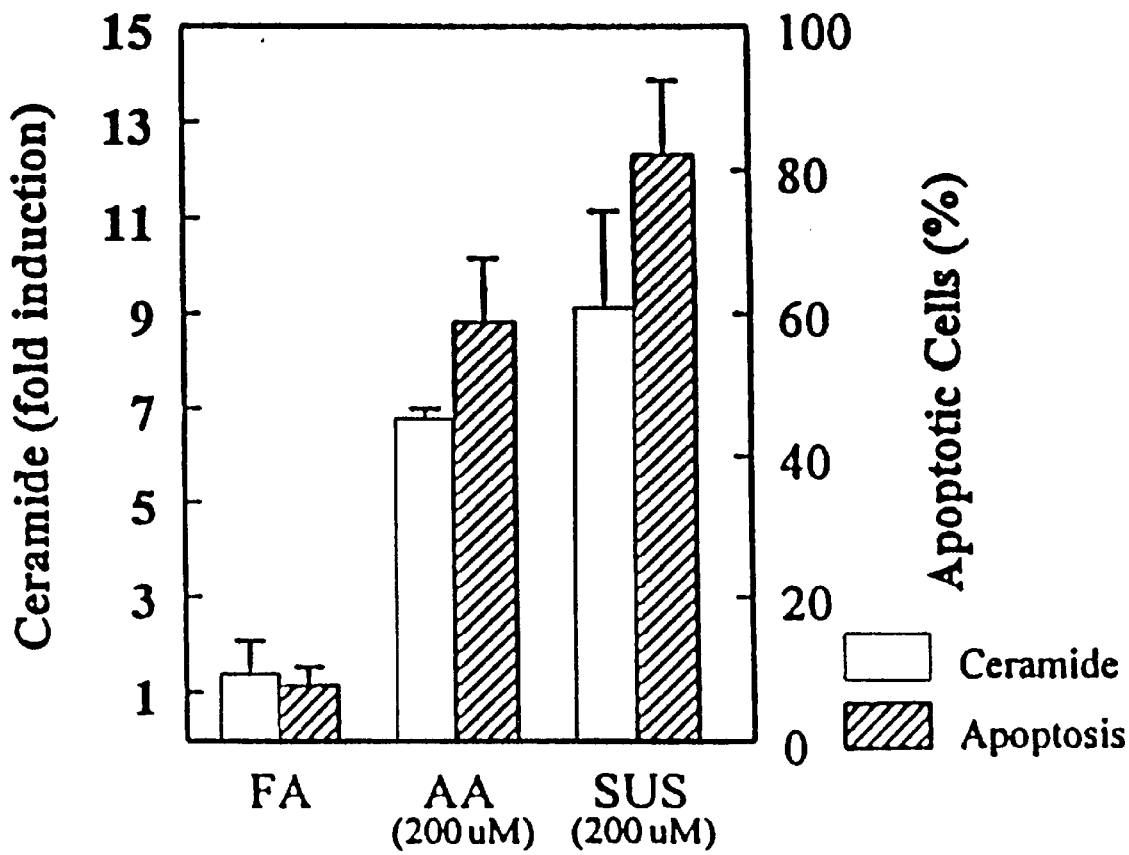

ND: 5,874,235

SCREENING ASSAYS FOR CANCER CHEMOPREVENTATIVE AGENTS

The U.S. Government has a paid-up license in this invention and the right in limited circumstances to require the patent owner to license others on reasonable terms as provided for by the terms of CA57345 awarded by the National Institutes of Health.

TECHNICAL AREA OF THE INVENTION

The invention relates to the area of cancer chemopreventative agents. More particularly, the invention relates to the area of screening assays for cancer chemopreventative agents.

BACKGROUND OF THE INVENTION

Because common epithelial cancers have resisted most therapeutic efforts, much hope is currently placed in chemoprevention (1). Chemopreventative measures are especially important in patients who are at elevated risk for neoplasia due to genetic or environmental factors. Though research on such agents is now blossoming, only a few compounds have been shown to be useful in vivo. Among these are nonsteroidal anti-inflammatory drugs (NSAID), which are effective in reducing colon tumors in genetically susceptible humans (2) and rodents (3,4). Additionally, epidemiological studies have determined that NSAID administration among the general population is associated with a reduced risk of colon cancer death (5).

Further progress in this area will in part depend on understanding the mechanisms by which such chemopreventative agents exert their protective effects. It is already well known that NSAID can inhibit cyclooxygenases (COX) (reviewed in 6), and some studies have shown that NSAID can induce apoptosis (also called programmed cell death or PCD) (7). Moreover, expression of COX-2 is elevated in colorectal tumors (8) and can protect intestinal epithelial cells from apoptosis (9). However, the biochemical mechanisms by which the NSAID and COX alter colonic cell proliferation have been largely unknown (reviewed in 10).

An understanding of the mechanisms by which known chemopreventative agents protect against tumors may lead to new methods of screening for other agents that are effective in preventing or treating cancers (cancer chemopreventative agents). There is a continuing need in the art for chemopreventative and chemotherapeutic agents.

SUMMARY OF THE INVENTION

It is an object of the invention to provide methods of screening for potential cancer chemopreventative agents. This and other objects of the invention are provided by one or more of the embodiments described below.

One embodiment of the invention provides a method of screening for potential cancer chemopreventative agents in which a cell is contacted with a test compound. The amount of arachidonic acid in the cell is then measured. A test compound which increases the amount of arachidonic acid in the cell is a potential cancer chemopreventative agent.

Another embodiment of the invention provides a method of screening for potential cancer chemopreventative agents in which a cell is contacted with a test compound. The amount of ceramide in the cell is then measured. A test compound which increases the amount of ceramide in the cell is a potential cancer chemopreventative agent.

Still another embodiment of the invention provides a method of screening for potential cancer chemopreventative agents in which a cell is contacted with a test compound. The amount of sphingomyelin in the cell is then measured. A test compound which decreases the amount of sphingomyelin in the cell is a potential cancer chemopreventative agent.

Yet another embodiment of the invention provides a method of screening for potential cancer chemopreventative agents in which a cell is contacted with a test compound. The amount of sphingomyelinase activity in the cell is then measured. A test compound which increases the amount of sphingomyelinase activity in the cell is a potential cancer chemopreventative agent.

Another embodiment of the invention provides a method of screening for potential cancer chemopreventative agents in which a cell is contacted with a test compound. The amount of phospholipase A2 activity in the cell is then measured. A test compound which increases the amount of phospholipase A2 activity in the cell is a potential cancer chemopreventative agent.

Yet another embodiment of the invention provides a method of screening for potential cancer chemopreventative agents in which a cell is contacted with a test compound. The amount of ceramide choline-phosphotransferase activity in the cell is then measured. A test compound which decreases the amount of ceramide choline-phosphotransferase activity in the cell is a potential cancer chemopreventative agent.

Even another embodiment of the invention provides a method of screening for potential cancer chemopreventative agents in which sphingomyelinase is contacted with a test compound. Sphingomyelinase activity is then measured. A test compound which increases sphingomyelinase activity is a potential cancer chemopreventative agent.

Still another embodiment of the invention provides a method of screening for potential cancer chemopreventative agents in which phospholipase A2 is contacted with a test compound. Phospholipase A2 activity is then measured. A test compound which increases the activity of phospholipase A2 is a potential cancer chemopreventative agent.

A further embodiment of the invention provides a method of screening for potential cancer chemopreventative agents in which ceramide choline-phosphotransferase is contacted with a test compound. Ceramide choline-phosphotransferase activity is then measured. A test compound which decreases the activity of ceramide choline-phosphotransferase is a potential cancer chemopreventative agent.

The present invention thus provides the art with methods of screening for potential cancer chemopreventative agents. Screening assays can be performed either in intact cells or in cell-free assay systems.

BRIEF DESCRIPTION OF THE DRAWINGS

In FIG. 1A, HCT116 and SW480 cells were treated with indomethacin (INDO) (300 $\mu$M) or SUS (125 $\mu$M for HCT116 and 200 $\mu$M for SW480 cells). Cells were collected at the indicated times, fixed and stained with Hoechst 33258 (23). The cells were counted and those with fragmented nuclei were scored as apoptotic. In FIG. 1B, HCT116 and SW480 cells were treated with SUS or INDO for 60 hours, harvested and stained as described above. Cells treated with SUS or INDO show the hallmarks of apoptosis.

FIG. 2A demonstrates that cycloheximide (CHX) inhibits SUS-induced apoptosis in HCT116 and SW480 cells. Cells were treated with the indicated combination of SUS (same concentrations as in FIG. 1) and CHX (10 µM). Apoptotic cells were evaluated as described in the legend to FIG. 1. FIG. 2B demonstrates that prostaglandin $E_2$ does not inhibit SUS-induced apoptosis. Cells were treated with the indicated combination of SUS (same concentrations as in FIG. 1) and prostaglandin $E_2$ (PGE, 10 µM).

In FIG. 3A, ceramide increases in a dose-dependent fashion in colon cancer cells treated with SUS or INDO. HCT116 and SW480 cells were treated with the indicated concentration of SUS and INDO for 48 hours. Cells were harvested and ceramide was quantified. The first lane of each panel corresponds to a ceramide standard (ceramide type III, Sigma). FIG. 3B demonstrates ceramide induction in HCT116 cells with increasing concentrations of SUS. FIG. 3C demonstrates ceramide induction in SW480 cells with increasing concentrations of SUS. FIG. 3D demonstrates ceramide induction in HCT116 cells with increasing concentrations of INDO. FIG. 3E demonstrates ceramide induction in SW480 cells with increasing concentrations of INDO. HCT116 and SW480 cells were treated with SUS or INDO as indicated. Ceramide levels were determined as described above. Data shows mean of at least two experiments with the error bars corresponding to the standard deviation. DMSO vehicle controls (using equivalent volumes) were performed in parallel with the drug treatments; no significant ceramide induction resulted (not shown). FIG. 3F demonstrates the time course of ceramide induction in HCT116 cells with increasing concentrations of SUS or INDO. FIG. 3G demonstrates the time course of ceramide induction in SW480 cells with increasing concentrations of SUS or INDO. HCT116 and SW480 cells were treated with SUS (125 µM for HCT116 and 200 µM for SW480) or INDO (300 µM). Control cells were treated with DMSO vehicle only. Cells were harvested at the indicated times following treatment and ceramide levels were determined as described above. The data are plotted as the mean of at least two experiments with the error bars corresponding to the standard deviation.

FIGS. 4A, 4B, 4C, 4D, 4E and 4F. The role of arachidonic acid in NSAID-mediated apoptosis. FIG. 4A demonstrates increased arachidonic acid levels in HCT116 cells after NSAID treatment. FIG. 4B demonstrates increased arachidonic acid levels in SW480 cells after NSAID treatment. HCT116 and SW480 cells were treated with the indicated concentrations of SUS or INDO. Arachidonic acid (AA) levels were determined by measuring release of $^3$H-AA into the media as previously described (18). Data are indicated as the mean of three replicates with the error bars corresponding to the standard deviation. In addition, the nature of the released radiolabeled material was evaluated by thin layer chromatography as previously described (28). Analysis of material released 24 hours after SUS or indomethacin treatment revealed only arachidonic acid. FIG. 4C demonstrates induction of sphingomyelin turnover in HCT116 cells in response to NSAID treatment. FIG. 4D demonstrates induction of sphingomyelin turnover in SW480 cells in response to NSAID treatment. HCT116 and SW480 cells were incubated with $^3$H-choline chloride (0.5 mCi ml$^{-1}$, 80 Ci mmol$^{-1}$, New England Nuclear) for 48 hours. After labeling, cells were washed with HBSS (Gibco) and treated with SUS or INDO for the indicated times. Sphingomyelin measurements were performed using the bacterial sphingomyelinase method as previously described (18). Sphingomyelin levels at each time point are plotted as a percentage of that in untreated control cells. For each point, the mean of at least two independent experiments is presented with the error bars corresponding to the standard deviations. FIG. 4E demonstrates that arachidonic acid can mimic the effects of SUS treatment. SW480 cells were treated with 200 µM arachidonic acid (AA), SUS (SUS) or behenic acid as a control fatty acid (FA) as indicated. FIG. 4F demonstrates that arachidonic acid and SUS act synergistically to induce ceramide increases and apoptosis. SW480 cells were treated with suboptimal doses (100 µM) of arachidonic acid (AA), SUS (SUS), or both (AA+SUS) as indicated. After 48 hours of treatment, apoptosis and ceramide increases were assessed as described for FIGS. 1 and 3, respectively. Ceramide increases (left axis) were expressed as fold increases relative to untreated cells. Apoptosis (right axis) was expressed as percent apoptotic cells minus percent apoptotic cells in untreated cells (5.6%+/−2.4). Data are indicated as the mean of duplicates with the error bars corresponding to the standard deviation.

DETAILED DESCRIPTION OF THE PREFERRED EMBODIMENTS

Figure 1A:
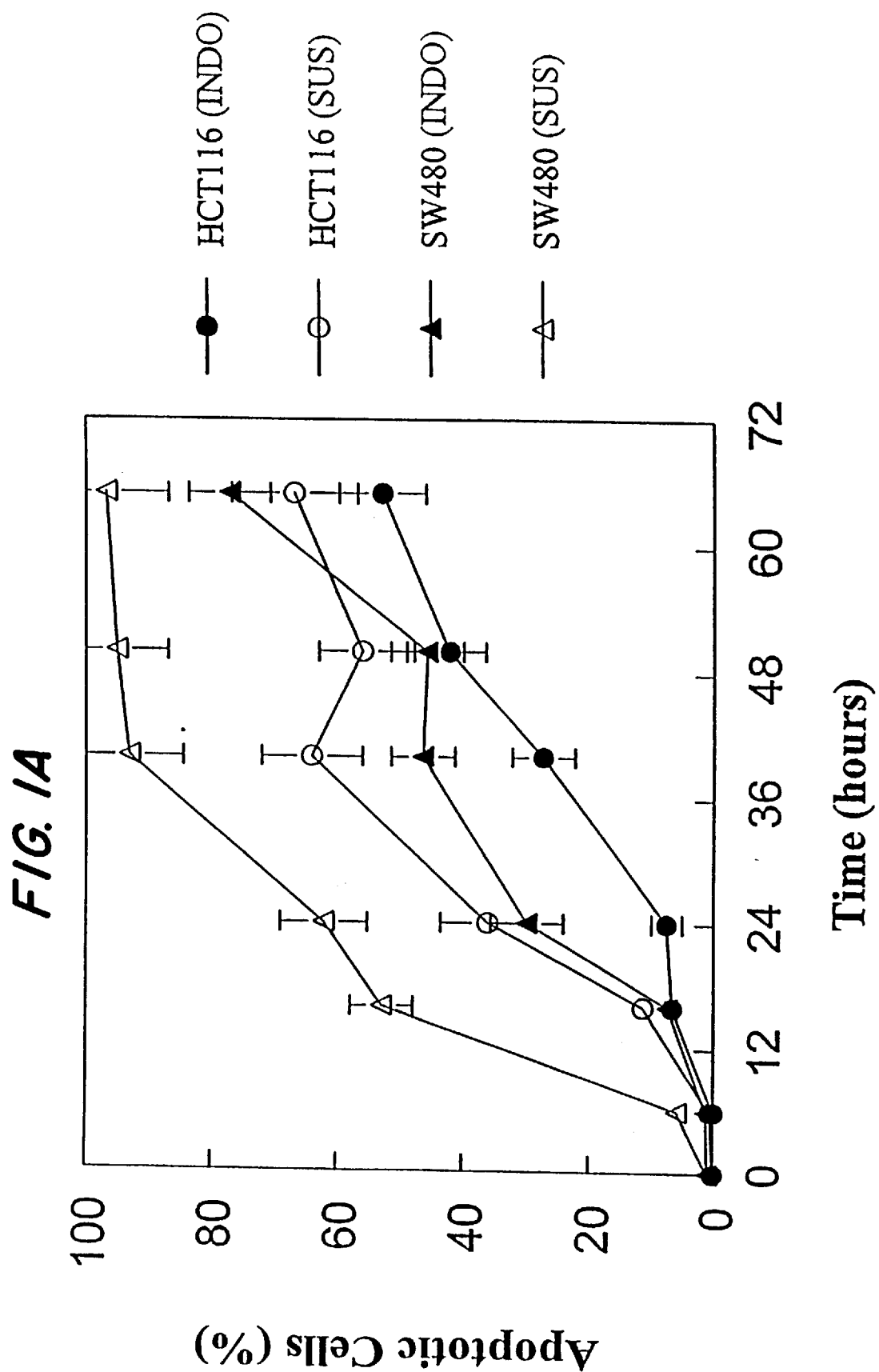
FIGS. 1A, 1B and 1C NSAID induce apoptosis in human colorectal cancer cells.

The inventors have discovered that treatment of colon cancer cells with nonsteroidal anti-inflammatory drugs induces apoptosis by inducing a dramatic increase in ceramide. The ceramide increase is mediated by elevated arachidonic acid levels resulting from cyclooxygenase inhibition. The elevated arachidonic acid levels stimulate sphingomyelinase.

To screen test compounds for potential cancer chemopreventative activity one can assay for the ability to increase cellular levels of arachidonic acid, ceramide, and/or sphingomyelin. Alternatively one can assay for the ability to increase the activities of sphingomyelinase or phospholipase A2. Another option is to assay for the ability of a test compound to decrease the activity of ceramide choline-phosphotransferase. Enzyme activities may be measured after contacting cells with a test compound or by contacting the enzyme with a test compound in a cell-free system. Any single or combination of these methods may be employed to screen compounds as potential therapeutic agents or prophylactic agents. Control assays measure cells or enzymes which have not been contacted with a test compound. Comparison of contacted to non-contacted cells or enzymes allows one to determine increases or decreases in metabolite levels or enzyme activity.

Cells that are contacted with test compounds may be either normal or tumor cells. They may derive from a cell line or may be freshly isolated from an animal or a human. Epithelial cells, such as glandular skin appendages (sudoriparous, sebaceous, or mammary glands), skin epidermis, corneal epithelium, alimentary tract lining, liver, pancreas, gastric and intestinal glands, exocrine and endocrine glands, peritoneal cavity linings, linings of the blood and lymph vessels, fibroblasts, and keratinocytes are particularly suitable for use in this method. Epithelial tumor cells, such as breast, epidermal, liver, pancreatic, gastric, intestinal, exocrine, endocrine, or lymphatic tumor cells, may also be used in this method. In a preferred embodiment, primary colorectal tumor cells or colorectal tumor cell lines, such as HCT116 and SW480, are used.

The test compounds may be pharmacologic agents already known in the art or may be compounds previously unknown to have any pharmacological activity. The compounds may be naturally occurring or designed in the laboratory. They may be isolated from microorganisms, animals, or plants, or may be produced recombinantly, or synthesized by chemical methods known in the art.

Assays for cellular components may be accomplished by any means known in the art. Arachidonic acid levels may be measured, for example, using mass spectroscopy, high performance liquid chromatography, or by determining the release of $^3$H-arachidonic acid into the culture medium as described by S. Jayadev et al. (18). In a preferred embodiment, a two- to three-fold increase in arachidonic acid levels is achieved 24 hours after exposure to a test compound. In a more preferred embodiment, a five-fold increase in arachidonic acid levels is achieved 48 hours after exposure to a test compound. Ceramide levels may be measured by, inter alia, using the *E. coli* diacylglycerol (DAG) kinase assay described by J. Preiss et al. (30). Sphingomyelin levels may be measured using the bacterial sphingomyelinase method described by Jayadev et al., supra, or by any other suitable method known in the art. In a preferred embodiment, sphingomyelin levels decrease by 40–50% 48 hours after exposure to a test compound.

Phospholipase A2, ceramide choline-phosphotransferase and sphingomyelinase, such as neutral sphingomyelinase, can be isolated from the appropriate tissue by standard biochemical methods. Cell-free assay systems for measuring a particular enzyme's activity may be prepared, for example, by mild homogenization in isotonic sucrose solution, mechanical breaking (i.e., grinding with sand or shaking with fine glass beads at high speed), ultrasonic or sonic oscillations, freezing and thawing, treatment with solvents (i.e., acetone), autolysis, or lysis with added enzymes. The enzymes can be purified by any single or combination of techniques, including size exclusion chromatography, ammonium sulfate fractionation, ion exchange chromatography, affinity chromatography, crystallization, or preparative gel electrophoresis. Enzyme reactions may be followed by spectrophotometric, manometric, decolorization, electrode, polarimetric, or chromatographic methods, or by chemical estimations. Specifically, sphingomyelinase activity may be measured, for example, by measuring the rate of hydrolysis of $^{14}$C-labelled sphingomyelin, or by mixed micellar assay (T. Okazaki et al., *J. Biol. Chem.* 269, 4070 (1994). Phospholipase A2 activity may be measured by, inter alia, measurement of $^3$H-arachidonic acid by radiochemical assay (Periwal et al., *Prostaglandins* 51, 191, 1996), fluorescence-based assay (S. G. Blanchard et al., *Anal. Biochem.* 222, 435, 1994), the Dole assay (M. Sano et al., *Fertil. Steril.* 61, 657, 1994), photometric micelle assay or *E. coli*-based assay (J. Aufenanger et al., *Eur. J. Clin. Chem. Clin. Biochem.* 31, 777, 1993), or reverse-phase high-performance liquid chromatographic assay (H. Tojo et al., *J. Lipid Res.* 34, 837, 1993). Ceramide choline-phosphotransferase activity may be measured, for example, as taught in E. P. Kennedy, *Meth. Enz.* 5, 486, 1962. Preferably, levels of sphingomyelinase, phospholipase A2, or ceramide choline-phosphotransferase activity decrease by 90% after 6 hours and 92% after 16 hours exposure of the enzyme to a test compound.

The teachings of each reference disclosed in this specification are incorporated by reference herein. The following examples are provided for exemplification purposes only and are not intended to limit the scope of the invention which has been described in broad terms above.

EXAMPLE 1

This example demonstrates the ability of sulindac sulfide to induce cell death.

The most extensively investigated NSAID for chemoprevention is sulindac, which can reduce the size and number of colorectal tumors in Familial Adenomatous Polyposis (FAP) patients (2) as well as in mouse models of FAP (4). We attempted to determine whether the active metabolite of sulindac, sulindac sulfide (SUS), could induce the death of commonly used colorectal cancer cell lines (HCT116 and SW480) at physiologically relevant drug concentrations.

Figure 1B:
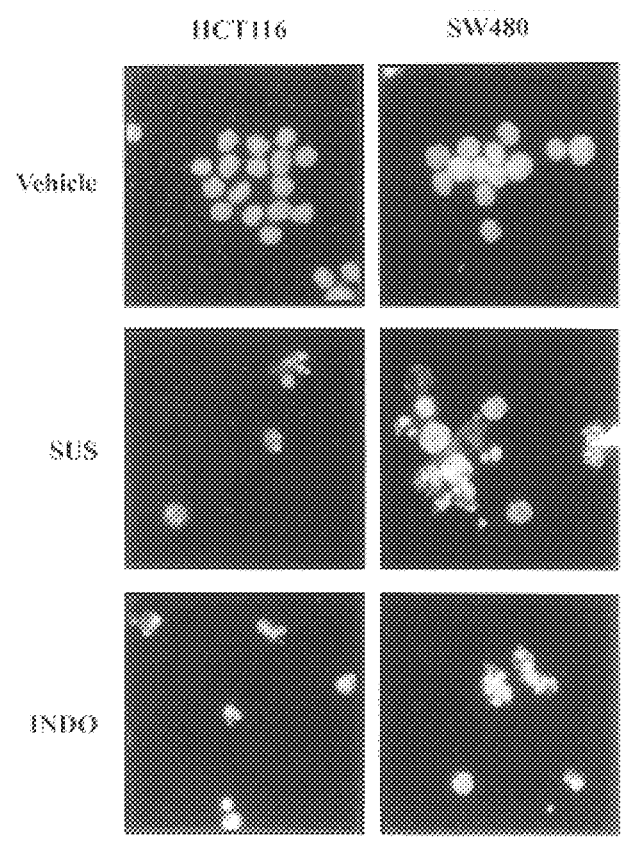
Figure 1C:
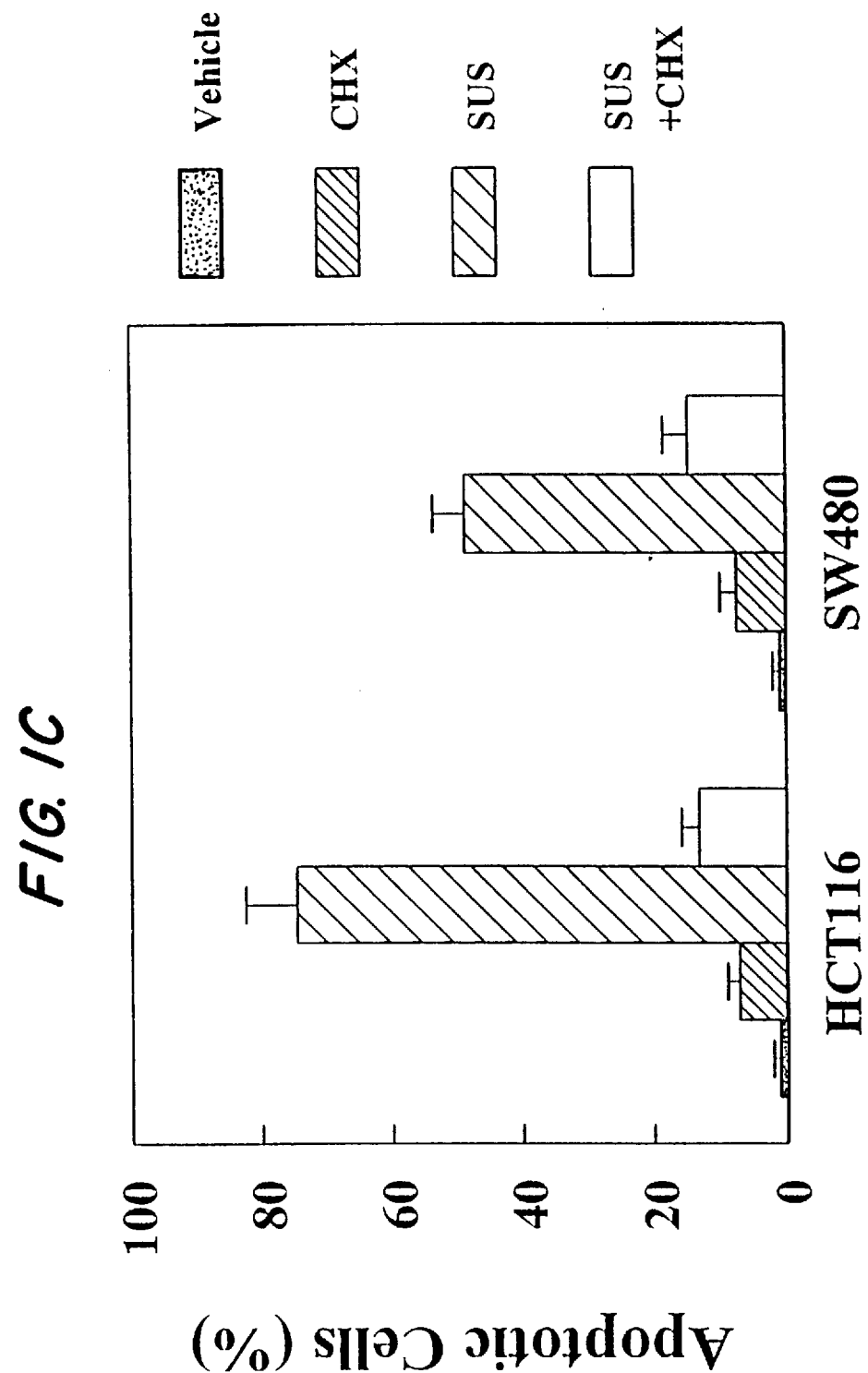

SUS resulted in death of both lines in a dose and time-dependent fashion, consistent with previous studies (7). At concentrations of 125 $\mu$M and 200 $\mu$M SUS in HCT116 and SW480 cells, respectively, the majority of cells died within 48 hours (FIG. 1A). This death appeared to be apoptotic, as it was accompanied by nuclear condensation and fragmentation (FIG. 1B) and exposure of phosphatidylserine groups on the cell surface, two hallmarks of apoptosis (11, 12).

SUS treatment of HCT and SW480 cells resulted in substantial phosphatidylserine exposure indicative of membrane unpacking. Phosphatidylserine exposure was assessed by merocyanine staining as previously described (31). Forty-eight hours after treatment with 125 $\mu$M SUS, 44% of HCT116 stained with merocyanine versus 4% in the vehicle-treated control cells. Likewise, 74% of SW480 cells stained with merocyanine 50 hours after treatment with 200 $\mu$M SUS versus 1.5% of the vehicle-treated control cells.

Thus, SUS induces cell death in colorectal cancer cell lines at physiologically relevant concentrations.

EXAMPLE 2

This example demonstrates that SUS-induced cell death is apoptotic.

Though the morphology of SUS-treated cells was consistent with apoptotic cell death, other cell death processes can mimic these changes. To demonstrate more definitively that SUS can actually induce apoptosis, we employed the criteria originally used to distinguish apoptosis from other death processes, namely, the requirement for macromolecular synthesis (11).

Figure 2A:
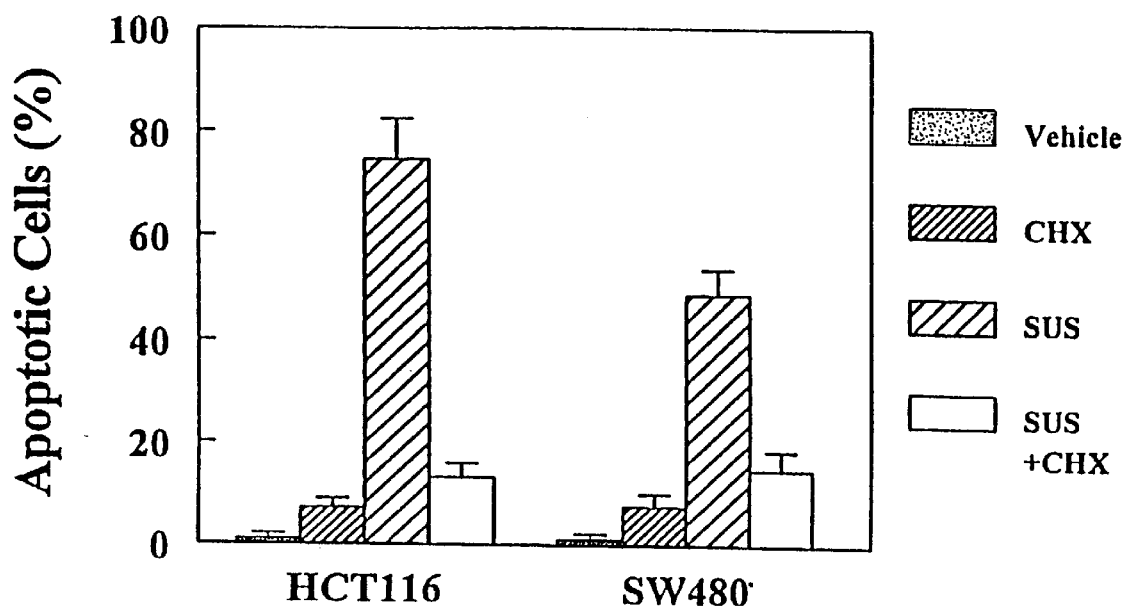
FIGS. 2A and 2B Effects of cycloheximide and prostaglandin $E_2$ on SUS-induced apoptosis.

We found that inhibition of protein synthesis by cycloheximide (CHX) (FIG. 2A), or of RNA synthesis by actinomycin D (not shown), could completely inhibit apoptosis at the concentrations of SUS used in the experiments shown in FIG. 1A. Interestingly, cycloheximide could not inhibit SW480 cell death at higher concentrations of SUS (not shown). This suggests that SUS can kill cells by two mechanisms: apoptosis at relatively low concentrations and non-specific toxic effects at higher concentrations. Such non-specific toxicity at high concentrations of pharmaceutical compounds is not unusual (13), and may have confounded some previous studies of NSAID action. Therefore, all subsequent analyses were performed using SUS concentrations that resulted in bona fide apoptosis.

EXAMPLE 3

This example demonstrates that SUS dramatically increases the production of ceramide in colorectal cancer cell lines.

Figure 2B:
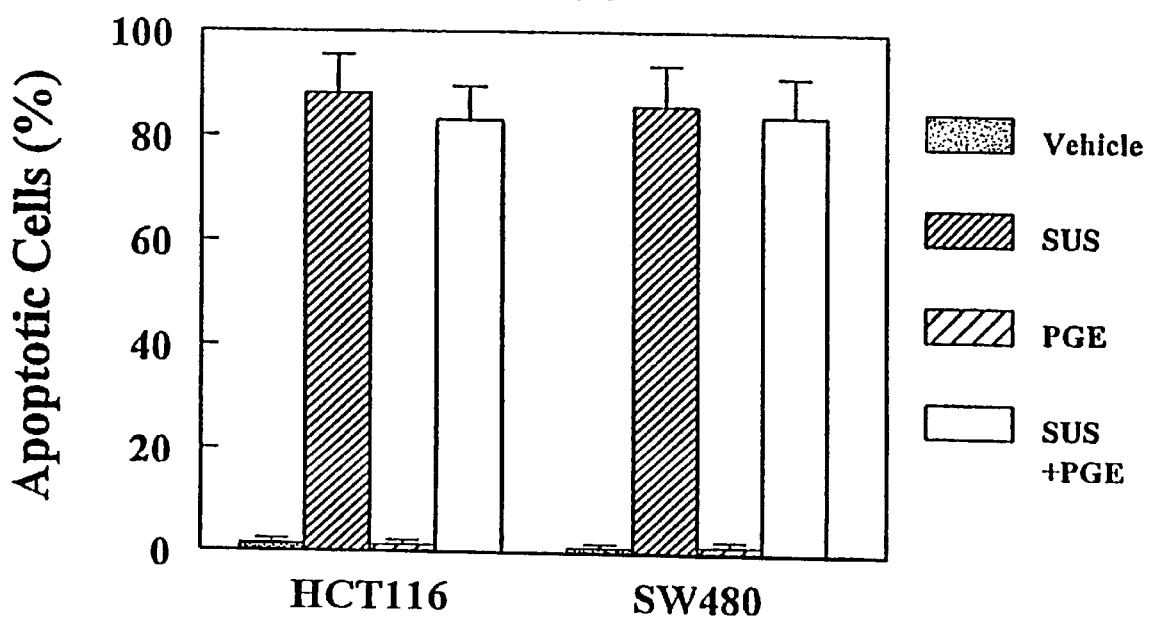

To investigate the mechanism by which SUS results in apoptosis, we first considered the previously suggested possibility that sulindac functions through inhibiting the production of growth-promoting prostaglandins by COX (8, 14, 15). To test this idea, we treated cells with both SUS and prostaglandin $E_2$ ($PGE_2$), the major COX product produced by colonic tumors (15). No inhibition of apoptosis was observed (FIG. 2B), consistent with previous studies which suggested that prostaglandins do not affect NSAID-induced death (16). We therefore investigated an alternative hypothesis: SUS might induce apoptosis through the production of ceramide.

Ceramide levels were measured using the *Escherichia coli* diacylglycerol (DAG) kinase assay as previously described (30) with the following modifications. After the initial lipid extraction, phases were broken by adding 2 ml chloroform and 2 ml 1M NaCl and lipids were washed with 1M NaCl prior to drying under nitrogen (32, 33). After solubilization, samples were sonicated for 15 seconds. The DAG reaction was performed for 30 minutes at 25° C. in a 100 µl reaction volume with 3.5 µg DAG kinase (Calbiochem) and 30 mCi $\gamma^{32}$P-ATP (Dupont NEN, 6000 Ci/mmol). After extraction of the labeled lipids, the lower chloroform phase was washed with 1% HCl prior to drying under nitrogen. The solvent mixture for thin layer chromatography was chloroform:acetone:methanol:acetic acid:water (10:4:3:2:1). Samples were quantitated using a Phosphorimager (Molecular Dynamics).

Figure 3A:
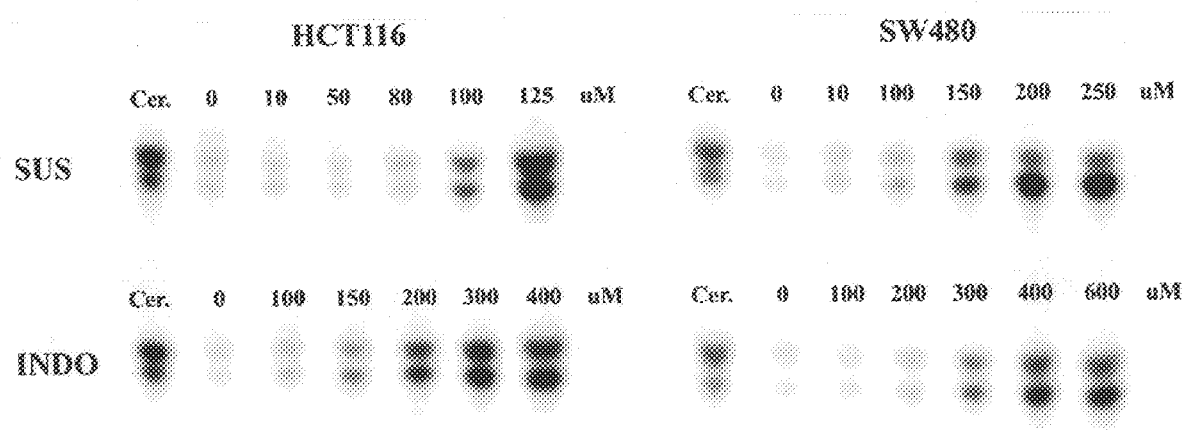
FIGS. 3A, 3B, 3C, 3D, 3E, 3F and 3G NSAID treatment induces ceramide generation.
Figure 3B:
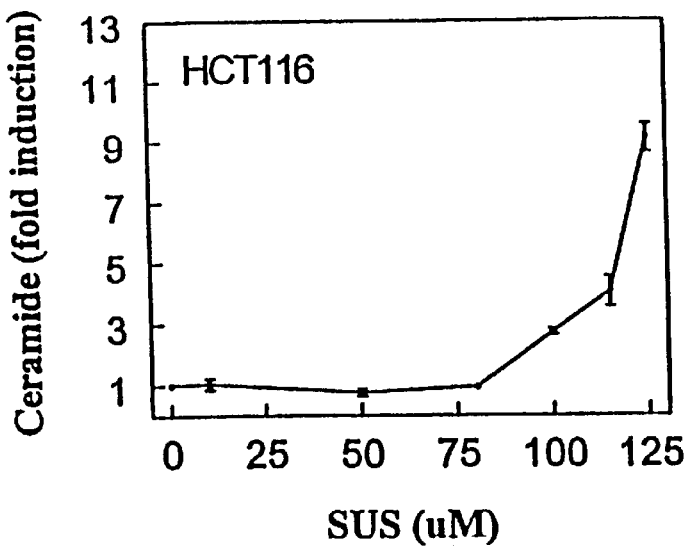
Figure 3D:
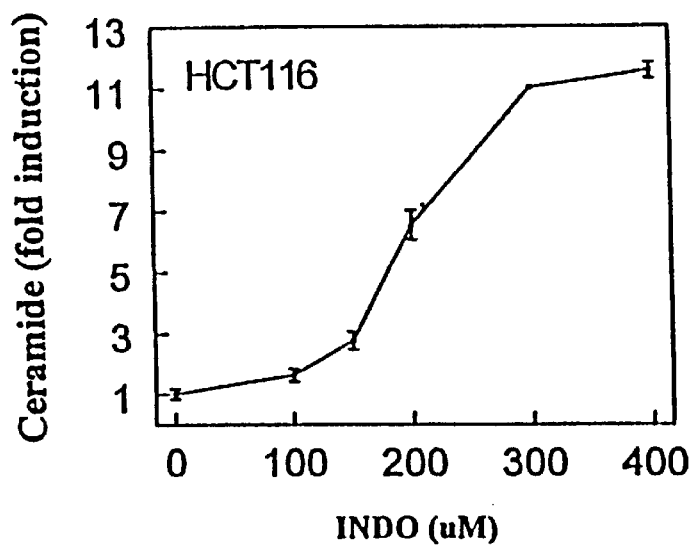
Figure 3F:
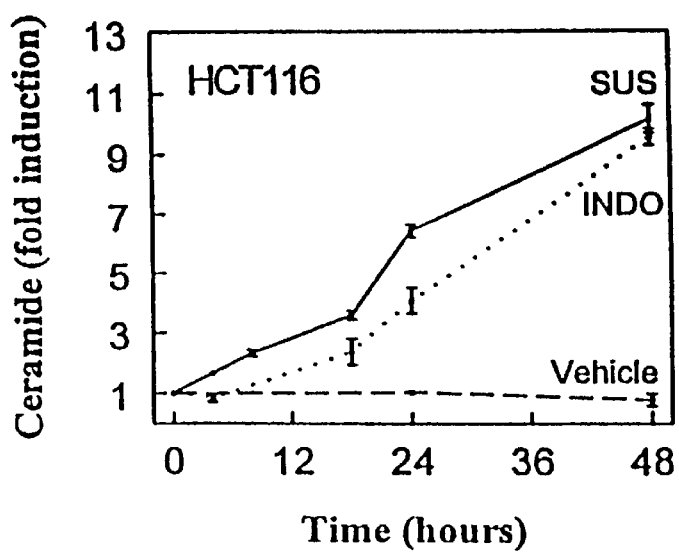
Figure 3C:
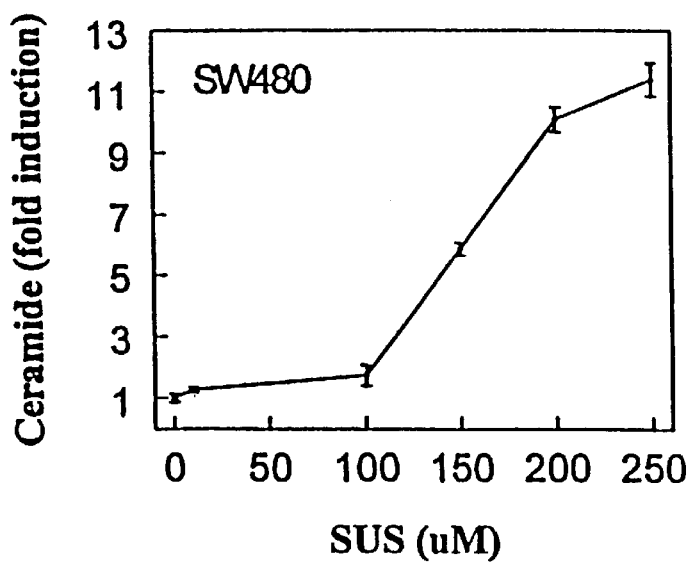
Figure 3E:
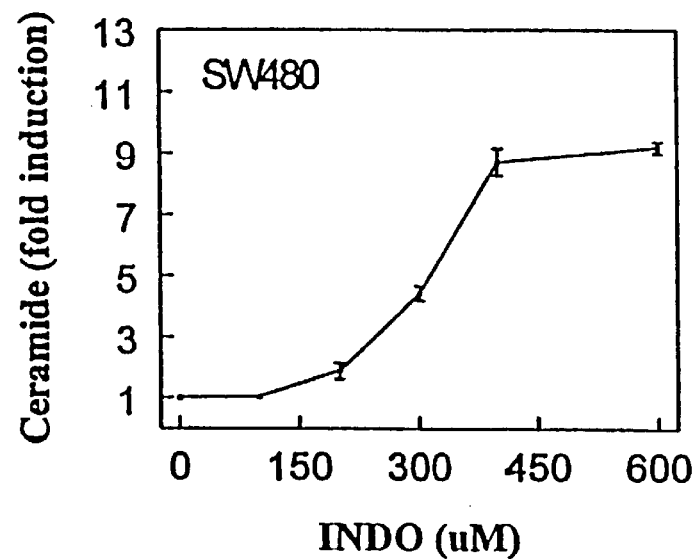
Figure 3G:
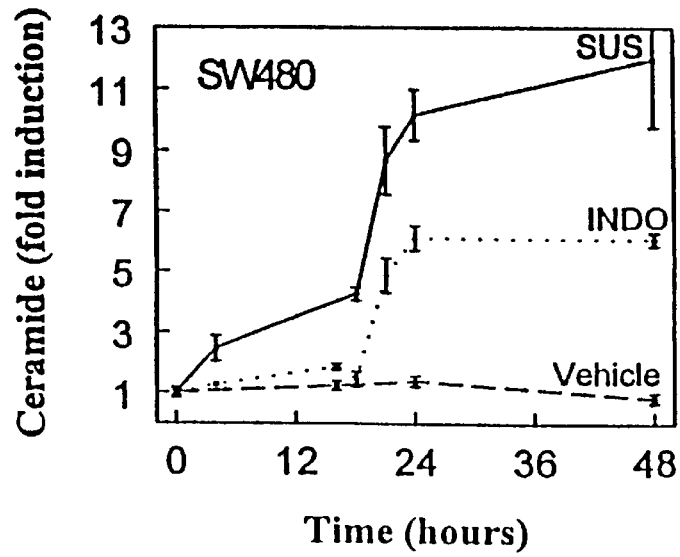

We found that SUS dramatically stimulated the production of ceramide in both cell lines tested (FIGS. 3A–3C), with maximum induction at 24 to 48 hours (FIGS. 3F and 3G). The magnitude of the ceramide increase was especially impressive (10-fold), as the induction of ceramide in other apoptotic systems is generally much less (17). There was also a remarkable threshold in the SUS doses required for these responses. At a concentration of 125 µM, SUS induced both cell death and ceramide in HCT116 cells (FIG. 3B), but at 50 µM, SUS induced neither. Similarly, SUS at 200 µM, but not at 100 µM, induced both ceramide and cell death in SW480 cells (FIG. 3C). Furthermore, the thresholds for ceramide induction were highly correlated with COX inhibition in these two lines. In HCT116 cells, 125 µM SUS reduced COX activity to 21+/−15% of controls (P=0.0017, one tailed Student's t-test) and induced ceramide and apoptosis. In contrast, 50 µM SUS did not substantially affect COX activity (98+/−30% relative to controls, P=0.95) and did not induce ceramide or apoptosis. Likewise, in SW480 cells, 200 µM SUS reduced COX activity to 37+/−27% of controls (P=0.02) and induced ceramide and apoptosis, whereas 50 µM SUS only reduced COX activity to 74+/−22% (P=0.16) and did not induce ceramide. Finally, additional control experiments demonstrated that the increase in ceramide was not simply the result of apoptosis. Three observations suggest that the ceramide increases were not the result of apoptosis. First, ceramide levels increased to substantial levels in SUS-treated cells as early as 8 hours post-treatment, when the cells were alive and lacked any morphologic features of apoptosis (i.e., nuclear fragmentation, membrane blebs). Second, cells treated with SUS and CHX do not undergo apoptosis but still have substantial increases in ceramide levels. HCT116 and SW480 cells were treated with 125 µM and 200 µM SUS respectively, with and without 10 µM CHX for 48 hours. Cells treated with SUS alone underwent apoptosis whereas cells treated with SUS and CHX did not. HCT116 and SW480 cells treated with SUS alone displayed a 10.0+/−0.4 and 9.2+/−0.1 fold increase in ceramide levels relative to vehicle controls, respectively. Likewise, HCT116 and SW480 cells treated with SUS in the presence of CHX exhibited a 5.1+/−0.5 and 7.9+/−1.3 fold increase in ceramide levels relative to controls, respectively. Third, apoptosis induced by other means in colon cells (p53 transferred by adenovirus infection) was not associated with a ceramide increase. p53 was over expressed in cells through infection with a recombinant adenovirus containing the p53 gene as previously described (34, 35). The p53-infected cells express p53 protein by 2 hours post-infection. In these cells, death begins at 24 hours, and at 48 hours 90–100% of the cells have undergone apoptosis. Adenovirus containing the β-galactosidase gene instead of the p53 gene was used as a control. Cells were harvested at 16 hours post-infection (when p53-virus infected cells express p53 but before the onset of apoptosis) and at 40 hours post-infection (when most cells are apoptotic). Relative to ceramide levels of β-galactosidase virus-infected cells, p53 virus-infected cells at 16 hours exhibited a ceramide level of 86.4+/−18.6%. At 40 hours post-infection, control virus-infected cells had a ceramide level of 81.4+/−12.3%, and p53 virus-infected cells exhibited a ceramide level of 85+/−8.3%.

Thus, the increase in ceramide in SUS-treated cells is a result of the SUS treatment itself, rather than the result of apoptosis.

EXAMPLE 4

This example demonstrates that SUS inhibition of COX activity leads to increases in arachidonic acid levels.

Figure 4A:
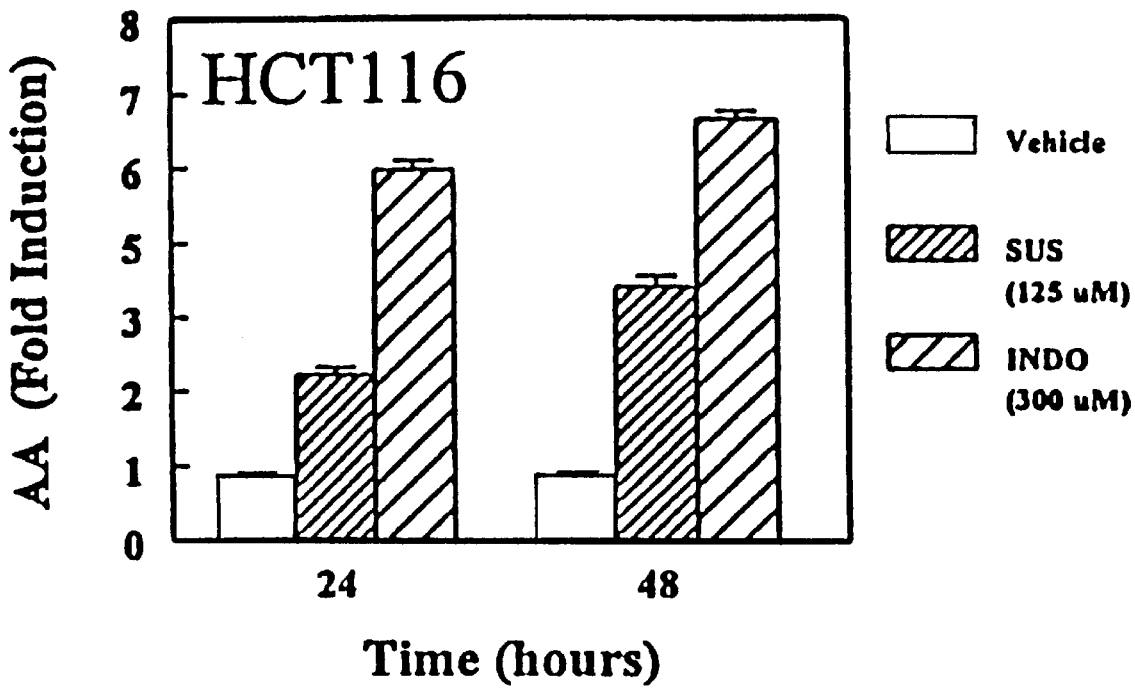
Figure 4B:
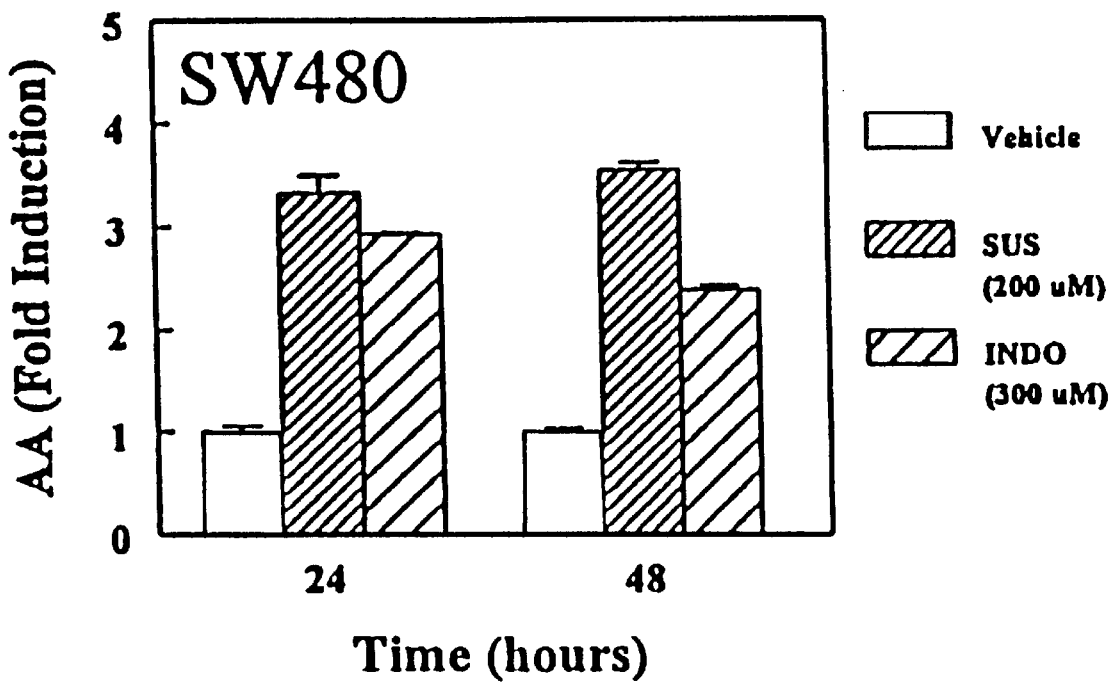

Arachidonic acid is known to stimulate neutral sphingomyelinase (18), which catalyzes the conversion of sphingomyelin to ceramide. We therefore considered the possibility that inhibition of COX activity might lead to increases in arachidonic acid, the substrate for COX. To test this hypothesis, we first determined whether SUS stimulated arachidonic acid accumulation. In both SW480 and HCT 116 cells, apoptosis-inducing doses of SUS increased arachidonic acid by 2 to 3 fold at 24 hours and by approximately 5 fold at 48 hours (FIGS. 4A and 4B). The arachidonic acid increase following SUS treatment was as great as that following treatment with mellitin, a known activator of phospholipase $A_2$. Arachidonic acid levels in HCT116 cells increased 3.5 fold one hour after treatment with 1 µM mellitin. Likewise, arachidonic acid levels increased 2.9 fold in SW480 cells one hour after mellitin treatment. Arachidonic acid (AA) levels were determined by measuring release of $^3$H-AA into the media as previously described (18). The nature of released radiolabeled material was evaluated by thin layer chromatography analysis as previously described (28). Analysis of material released 24 hours after treatment with 1 $\mu$M or 2.5 $\mu$M mellitin revealed only arachidonic acid.

Doses of SUS slightly lower than required to induce apoptosis failed to induce arachidonic acid release. Treatment of HCT116 cells with 50 $\mu$M SUS did not substantially increase arachidonic acids levels (0.90, 1.05 and 1.14 relative to control after 8, 16 and 24 hours of treatment), nor did 50 $\mu$M SUS induce ceramide and apoptosis. The induction of apoptosis by other means (for example, treatment with ceramide) did not result in similar increases in arachidonic acid. Treatment with 200 $\mu$M SUS for 16 hours resulted in a 5.1 and 3.4 fold increase in arachidonic acid in HCT 116 and SW480 cells, respectively. At this time point, the majority of cells had not yet undergone apoptosis. In contrast, treatment with 100 $\mu$M ceramide for 16 hours resulted in nearly complete (>90%) induction of apoptosis but only modest (1.5 and 1.9 fold) increases in arachidonic acid in HCT116 and SW480 cells, respectively.

Thus, treatment with SUS at a concentration that induces apoptosis increases arachidonic acid levels.

EXAMPLE 5

This example demonstrates the effect of SUS treatment on sphingomyelin levels.

Figure 4D:
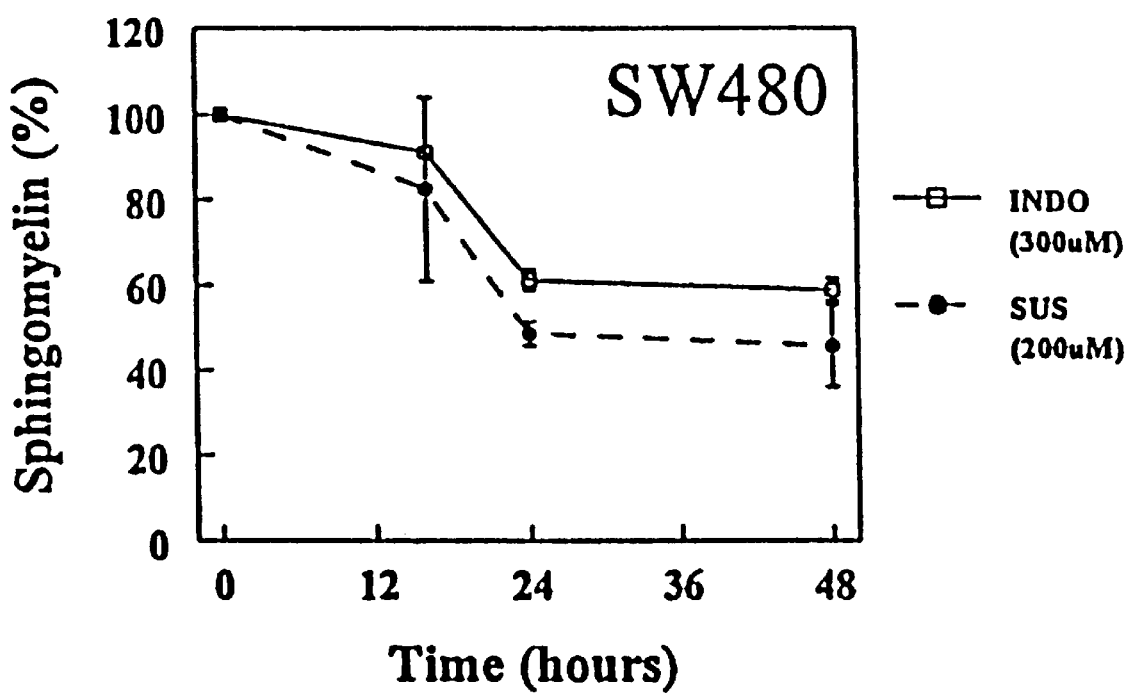

To test whether the increased ceramide was associated with evidence of augmented sphingomyelinase activity, we measured total sphingomyelin levels after SUS treatment. Sphingomyelin levels decreased by 40–50% at 48 hours after SUS treatment and, as with the other responses evaluated, suboptimal doses of SUS were inadequate to decrease sphingomyelin levels (FIGS. 4C and 4D). We also measured neutral sphingomyelinase activity in lysates from the treated cells and no differences were found. Neutral sphingomyelinase activity was assayed as described (18). After cell lysis, protein concentrations were determined using the Bradford method (Bio-Rad) and 200 mg cellular protein was used in each assay. Neutral sphingomyelinase activity was determined by measuring the rate of hydrolysis of $^{14}$C-labelled sphingomyelin (Amersham). SW480 and HCT116 cell lines were treated with SUS (50, 200, and 600 $\mu$M) for 6 to 24 hours.

None of these treatments enhanced neutral sphingomyelinase activity in cell lysates. In a typical experiment, treatment of HCT116 with 200 $\mu$M of SUS resulted in a neutral sphingomyelinase activity of 90% after 6 hours and 92% after 16 hours relative to untreated controls. This was consistent with the idea that it was not an increased concentration of enzyme, but rather an arachidonic acid-mediated stimulation of activity, that was responsible for the decrease in sphingomyelin and the increase in ceramide, because the interaction between arachidonic acid and neutral sphingomyelinase would not have been predicted to be preserved during preparation of cellular lysates (18).

EXAMPLE 6

This example demonstrates the ability of arachidonic acid to mimic the effects of SUS treatment.

Figure 4F:
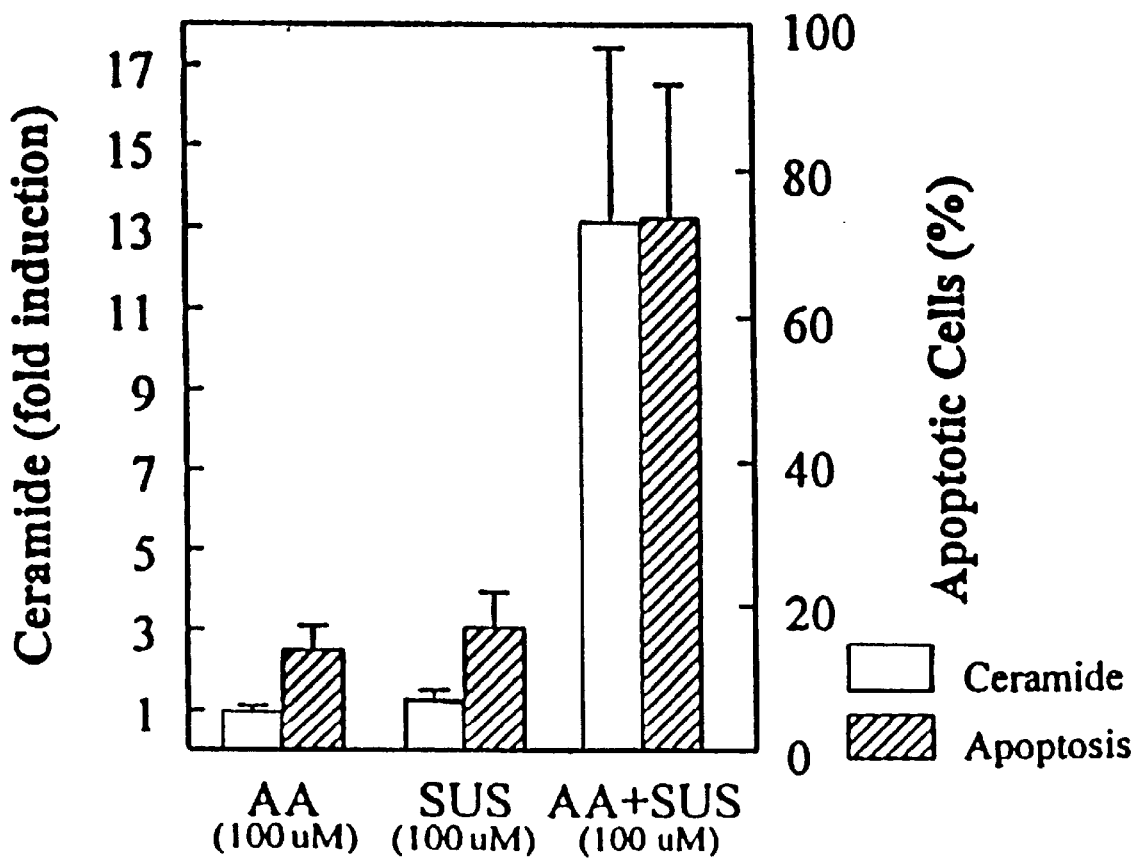

If increased arachidonic acid is the true mediator of sulindac's activity then arachidonic acid should mimic its effects. Accordingly, 200 $\mu$M arachidonic acid was a potent inducer of ceramide and apoptosis (FIG. 4E). In contrast, 200 $\mu$M behenic acid, a control fatty acid which is not a substrate for COX, had virtually no effect on ceramide levels and apoptosis. Moreover, the effects of suboptimal SUS and arachidonic acid treatment were synergistic for ceramide and apoptosis (FIG. 4F). For example, doses of arachidonic acid and SUS (100 $\mu$M each) that had little effect on ceramide levels separately resulted in over a ten fold increase in ceramide together. These results strongly support the role of arachidonic acid in SUS chemoprevention and virtually rule out the possibility that SUS functions by the classic prostaglandin-dependent mechanism described for NSAID in which an antagonistic rather than a synergistic response would be expected for arachidonic acid (6).

EXAMPLE 7

This example demonstrates the ability of indomethacin, another COX inhibitor, to mimic the effects of SUS treatment.

If our model for sulindac action is valid, the biochemical events described above would be predicted to be induced by any inhibitor of COX, not simply SUS. To test this prediction, we treated the cells with indomethacin, an NSAID structurally distinct from sulindac. Indomethacin was found to induce apoptosis, increase arachidonic acid and ceramide concentrations, and activate sphingomyelin hydrolysis to similar degrees as SUS in both cell lines (FIGS. 1A and 1B, 3A, and 3D–3G, and 4A–4D). For example, in SW480 cells, indomethacin induced 94% of the cells to undergo apoptosis in a cycloheximide sensitive manner, a 6-fold increase in ceramide levels, and a 3–4 fold increase in arachidonic acid.

Figure 5:
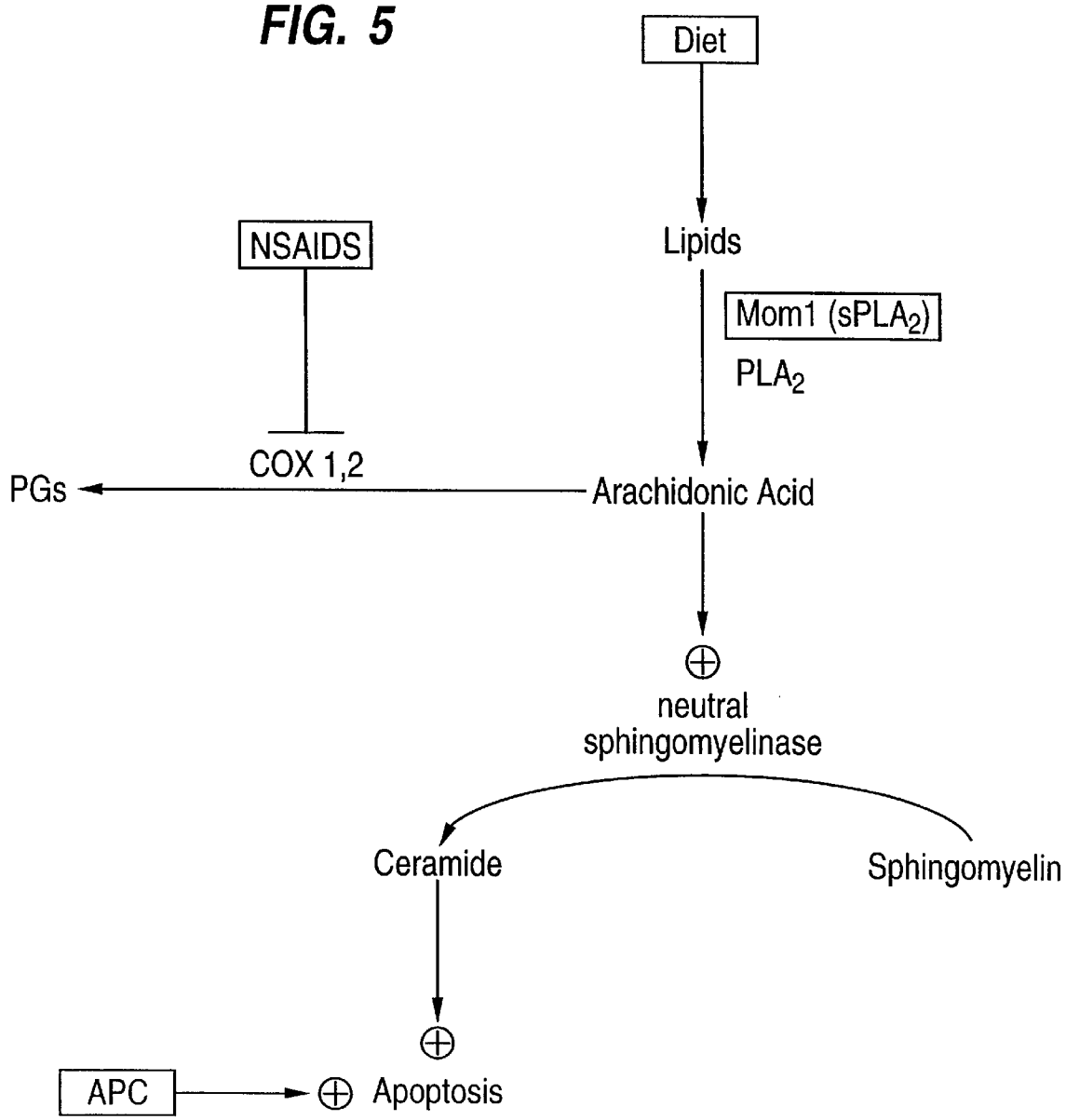
FIG. 5. Model relating arachidonic acid and ceramide to colorectal cancer chemoprevention. Mutation of the APC gene initiates colorectal tumorigenesis and results in abnormally decreased apoptosis (reviewed in 10, 22). Perturbation of lipid metabolism by pharmacological, dietary, or genetic means can partially correct the deficits. Arachidonic acid is generated by cytosolic and secreted phospholipase $A_2$, which hydrolyzes plasma membrane lipids or lipids derived from the diet. Arachidonic acid is normally used as a substrate by the cyclooxygenases to produce eicosanoids such as prostaglandins. NSAID inhibit the activity of the cyclooxygenases, which increases the cellular pool of arachidonic acid. Arachidonic acid stimulates sphingomyelinase activity (18), which catalyzes the hydrolysis of sphingomyelin to generate ceramide. Ceramide acts as second messenger that activates the cellular apoptotic machinery. The Mom1 gene is a modifier of polyp formation in the Min mouse, a model for APC. The Mom1 gene encodes a secreted phospholipase $A_2$, an enzyme predicted to increase the level of free arachidonic acid. Inactivating mutations in Mom1 predispose Min mice to developing intestinal polyps and would be expected to result in reduced levels of arachidonic acid (24). This in turn could result in decreased production of ceramide and therefore a relative resistance to programmed cell death and increased tumor susceptibility. The lipid compositions of diets are known to affect colon cancer risk (25) and apoptosis (29). Diets rich in unsaturated fatty acids such as arachidonic acid are associated with a decreased incidence of colon cancer (26). This effect could be due to increased levels of arachidonic acid and subsequent increased susceptibility to apoptosis as described above.

These results suggest a mechanism for the chemopreventative activity of NSAID (FIG. 5). We suggest that NSAIDs such as sulindac and indomethacin affect tumor growth by inhibiting COX activity, causing a build-up of the COX substrate arachidonic acid (FIGS. 4A and 4B), and activating sphingomyelinase activity (FIGS. 4C and 4D and 18) leading to production of the powerful apoptosis-inducer ceramide (FIG. 3). This ability of SUS is not limited to colon cancer cells; primary fibroblasts and immortalized keratinocytes can increase ceramide levels and undergo apoptosis in response to SUS. Treatment of primary human diploid fibroblast (HDF, Clonetics) and immortalized human keratinocytes, (HaCat, 36) with SUS resulted in dose-dependent induction of ceramide and apoptosis. Forty-eight hours after exposure to 200 $\mu$M SUS greater than 70% of the cells had undergone apoptosis and ceramide levels were 8.2 and 4.7 fold increased in HDF and HaCat cells, respectively. This is consistent with NSAIDs' ability to reduce tumor formation in a variety of tissues (19) and their adverse effects on normal gastric mucosa, but it fails to explain the apparent greater sensitivity of tumor cells. The in vivo effect will likely depend on the local concentration of the NSAID in the incipient tumor microenvironment as well as the target cell's "lipid biostat" (20). The fact that the concentration of SUS is higher in the intestines than in other organs, due to enterohepatic circulation and due to the metabolic activation of sulindac to SUS by gut flora (21), may be responsible for its particular efficacy in intestinal tumorigenesis.

This model links together several apparently disparate observations. Patients genetically predisposed to colorectal tumorigenesis have a defect in a gene (APC) (reviewed in 10, 22), which can induce apoptosis in neoplastic colorectal epithelium (23). The efficacy of sulindac in such patients may be attributable to its functional substitution for APC in such cells. It has also been shown that modification of lipid metabolism, through inherited mutation of genes encoding a secreted phospholipase, can dramatically alter tumor incidence in mice with germline mutations of APC (24), and that certain dietary lipids are correlated with colorectal cancer incidence in human populations (25, 26). Finally, recent studies with COX-2 null mice strongly implicate inhibition of COX activity as a critical effector of NSAID chemoprevention (27). All of these observations are consistent with the idea, summarized in FIG. 5, that lipids, in particular ceramide and arachidonic acid, play pivotal roles in protecting humans and mice from colorectal tumorigenesis through the control of apoptosis.

REFERENCES

1. B. Levin, *Curr Opin Oncol* 7, 397 (1995).
2. W. R. Waddell, G. F. Ganser, E. J. Cerise, R. W. Loughry, *Am J Surg* 157, 175 (1989); D. Labayle, et al., *Gastroenterology* 101, 635 (1991); J. Rigau, et al., *Ann Intern Med* 115, 952 (1991); F. M. Giardiello, et al., *N Engl J Med* 328, 1313 (1993); G. Winde, H. G. Gumbinger, H. Osswald, F. Kemper, H. Bunte, *Int J Colorectal Dis* 8, 13-7 (1993); W. Waddell, *J Surg Oncol* 55, 52 (1994).
3. M. Pollard, P. H. Luckert, *Science* 214, 558 (1981); M. Moorghen, et al., *J Pathol* 156, 341 (1988); M. Pollard, P. H. Luckert, *Cancer Res* 49, 6471 (1989); B. S. Reddy, C. V. Rao, A. Rivenson, G. Kelloff, *Carcinogenesis* 14, 1493 (1993).
4. Y. Beazer-Barclay, et al., *Carcinogenesis* 17, 1757 (1996); S. K. Boolbol, et al., *Cancer Research* 56, 2556 (1996); R. F. Jacoby, et aL, *Cancer Research* 56, 710 (1996).
5. G. A. Kune, S. Kune, L. F. Watson, *Cancer Res* 48, 4399 (1988); Rosenberg, et al, *J Natl Cancer Inst* 83, 355 (1991); M. J. Thun, M. M. Namboodiri, C. W. Heath, Jr., *N Engl J Med* 325, 1593 (1991); G. Gridley, et al., *J Natl Cancer Inst* 85, 307 (1993); R. F. Logan, J. Little, P. G. Hawtin, J. D. Hardcastle, *British Medical Journal* 307, 285 (1993); E. Giovannucci, et al., *Ann Intern Med* 121, 241 (1994); I. I. Peleg, H. T. Maibach, S. H. Brown, C. M. Wilcox, *Arch Intern Med* 154, 394 (1994).
6. J. R. Vane, *Br J Rheumatol* 35, 1 (1996); F. M. Giardiello, G. J. Offerhaus, R. N. DuBois, *Eur J Cancer* 31A, 1071 (1995).
7. G. A. Piazza, et al., *Cancer Res* 55, 3110 (1995); X. Lu, W. Xie, D. Reed, W. S. Bradshaw, D. L. Simmons, *Proc Natl Acad Sci USA* 92, 7961 (1995); P. Pasricha, et al., *Gastroenterology* 109, 994 (1995); S. J. Shiff, L. Qiao, L. L. Tsai, B. Rigas, *J Clin Invest* 96, 491 (1995); S. J. Shiff, M. I. Koutsos, L. Qiao, B. Rigas, *Exp Cell Res* 222, 179 (1996).
8. C. E. Eberhart, et al., *Gastroenterology* 107, 1183 (1994); H. Sano, et al., *Cancer Res* 55, 3785 (1995); W. Kutchera, et al., *Proc Natl Acad Sci USA* 93, 4816 (1996).
9. M. Tsujii, R. N. Dubois, *Cell* 83, 493 (1995).
10. S. M. Prescott, R. L. White, *Cell* 87, 783 (1996).
11. A. H. Wyllie, *Curr Opin GenetDev* 5, 97 (1995); C. B. Thompson, *Science* 267, 1456 (1995); X. M. Yin, Z. N. Oltvai, D. J. Veis-Novack, G. P. Linette, S. J. Korsmeyer, *Cold Spring Harb Symp Quant Biol* 59, 387 (1994).
12. V. A. Fadok, et aL, *J Immunol* 148, 2207 (1992); V. A. Fadok, et al., *Chest* 103, 102S (1993); S. J. Martin, et al., *J Exp Med* 182, 1545 (1995).
13. S. V. Lennon, S. J. Martin, T. G. Cotter, *Cell Prolif* 24, 203 (1991).
14. L. Qiao, et al., *Biochim Biophys Acta* 1258, 215 (1995).
15. B. Rigas, I. S. Goldman, L. Levine, *J Lab Clin Med* 122, 518 (1993).
16. R. Hanif, et al., *Biochem Pharmacol* 52, 237 (1996).
17. K. A. Dressler, S. Mathias, R. N. Kolesnick, *Science* 255, 1715 (1992); M. Verheij, et al., *Nature* 380, 75 (1996).
18. S. Jayadev, C. M. Linardic, Y. A. Hannun, *J Biol Chem* 269, 5757 (1994).
19. V. Hial, Z. Horakova, F. E. Shaff, M. A. Beaven, *Eur J Pharmacol* 37, 367 (1976); V. Hial, M. C. De Mello, Z. Horakova, M. A. Beaven, *J Pharmacol Exp Ther* 202, 446 (1977); A. Bennett, D. A. Berstock, M. A. Carroll, *Br J Cancer* 45, 762 (1982); T. Tanaka, T. Kojima, N. Yoshimi, S. Sugie, H. Mori, *Carcinogenesis* 12, 1949 (1991); P. Pepin, L. Bouchard, P. Nicole, A. Castonguay, *Carcinogenesis* 13, 341 (1992).
20. Y. A. Hannun, *Science* 274, 1855 (1996).
21. D. E. Duggan, K. F. Hooke, S. S. Hwang, *Drug Metab Dispos* 8, 241 (1980).
22. K. W. Kinzler, B. Vogelstein, *Cell* 87, 159 (1996).
23. P. J. Morin, B. Vogelstein, K. W. Kinzler, *Proc Natl Acad Sci USA* 93, 7950 (1996).
24. W. F. Dietrich, et al., *Cell* 75, 631 (1993); M. MacPhee, et al., *Cell* 81, 957 (1995); A. R. Moser, et al., *Proc Natl Acad Sci USA* 90, 8977 (1993); A. R. Moser, H. C. Pitot, W. F. Dove, *Science* 247, 322 (1990).
25. W. C. Willett, M. J. Stampfer, G. A. Colditz, B. A. Rosner, F. E. Speizer, *N Engl J Med* 323, 1664 (1990); E. Giovannucci, W. C. Willett, *Ann Med* 26, 443 (1994).
26. B. S. Reddy, *Cancer Metastasis Rev* 13, 285 (1994).
27. M. Oshima, et al., *Cell* 87, 803 (1996).
28. W. E. Lands, B. Samuelsson, *Biochim Biophys Acta* 164, 426 (1968).
29. C. O. Bellamy, R. D. Malcomson, D. J. Harrison, A. H. Wyllie, *Semin Cancer Biol* 6, 3 (1995).
30. J. Preiss et al., *J. Biol. Chem.* 261, 8597 (1986).
31. R. F. Ashman, D. Peckham, S. Alhasan, L. L. Stunz, *Immunology Letters* 48, 159 (1995).
32. P. P. Van Veldhoven, T. J. Matthews, D. P. Bolognesi, R. M. Bell, *Biochem Biophys Res Commun* 187, 209 (1992).
33. P. P. Van Veldhoven, R. M. Bell, *Biochim Biophys Acta* 959, 185 (1988).
34. K. Polyak, T. Waldman, T.-C. He, K. W. Kinzler, B. Vogelstein, *Genes & Development* 10, 1945 (1996).
35. W. S. El-Deiry, et al., *Cell* 75, 817 (1993).
36. P. Boukamp et al., *J. of Cell Biol.* 106, 761 (1988).

We claim:

1. A method of screening for potential cancer chemopreventative agents comprising the steps of:

contacting a fibroblast with a test compound; and measuring the amount of arachidonic acid in the fibroblast, a test compound which increases the amount of arachidonic acid in the fibroblast being a potential cancer chemopreventative agent.

2. A method of screening for potential cancer chemopreventative agents comprising the steps of:

contacting a cell with a test compound; and measuring the amount of ceramide in the cell, a test compound which increases the amount of ceramide in the cell being a potential cancer chemopreventative agent.

3. The method of claim 2 wherein the cell is an epithelial cell.

4. The method of claim 2 wherein the cell is a fibroblast.

5. The method of claim 2 wherein the cell is a keratinocyte.

6. The method of claim 2 wherein the cell is an epithelial tumor cell.

7. The method of claim 2 wherein the cell is a colorectal cancer cell.

8. A method of screening for potential cancer chemopreventative agents comprising the steps of:

contacting a cell with a test compound; and measuring the amount of sphingomyelin in the cell, a test compound which decreases the amount of sphingomyelin in the cell being a potential cancer chemopreventative agent.

9. The method of claim 8 wherein the cell is an epithelial cell.

10. The method of claim 8 wherein the cell is a fibroblast.

11. The method of claim 8 wherein the cell is a keratinocyte.

12. The method of claim 8 wherein the cell is an epithelial tumor cell.

13. The method of claim 8 wherein the cell is a colorectal cancer cell.

14. A method of screening for potential cancer chemopreventative agents comprising the steps of:

contacting a cell with a test compound; and measuring the amount of sphingomyelinase activity in the cell, a test compound which increases the amount of sphingomyelinase activity in the cell being a potential cancer chemopreventative agent.

15. The method of claim 14 wherein the cell is an epithelial cell.

16. The method of claim 14 wherein the cell is a fibroblast.

17. The method of claim 14 wherein the cell is a keratinocyte.

18. The method of claim 14 wherein the cell is an epithelial tumor cell.

19. The method of claim 14 wherein the cell is a colorectal cancer cell.

20. A method of screening for potential cancer chemopreventative agents comprising the steps of:

contacting a fibroblast with a test compound; and measuring the amount of phospholipase A2 activity in the fibroblast, a test compound which increases the amount of phospholipase A2 activity in the fibroblast being a potential cancer chemopreventative agent.

21. A method of screening for potential cancer chemopreventative agents comprising the steps of:

contacting a cell with a test compound; and measuring the amount of ceramide choline-phosphotransferase activity in the cell, a test compound which decreases the amount of ceramide choline-phosphotransferase activity in the cell being a potential cancer chemopreventative agent.

22. The method of claim 21 wherein the cell is an epithelial cell.

23. The method of claim 21 wherein the cell is a fibroblast.

24. The method of claim 21 wherein the cell is a keratinocyte.

25. The method of claim 21 wherein the cell is an epithelial tumor cell.

26. The method of claim 21 wherein the cell is a colorectal cancer cell.

27. A method of screening for potential cancer chemopreventative agents comprising the steps of:

contacting sphingomyelinase with a test compound; and measuring the amount of sphingomyelinase activity, a test compound which increases the amount of sphingomyelinase activity being a potential cancer chemopreventative agent.

28. A method of screening for potential cancer chemopreventative agents comprising the steps of:

contacting ceramide choline-phosphotransferase with a test compound; and measuring the amount of ceramide choline-phosphotransferase activity, a test compound which decreases the amount of ceramide choline-phosphotransferase activity being a potential cancer chemopreventative agent.

* * * * *